US 11,478,584 B2

(12) United States Patent
Oda et al.

(10) Patent No.: US 11,478,584 B2
(45) Date of Patent: Oct. 25, 2022

(54) MULTI-CHAMBER SYRINGE

(71) Applicant: CareFusion 303, Inc., San Diego, CA (US)

(72) Inventors: Todd Oda, Torrance, CA (US); George Mansour, Diamond Bar, CA (US); Eugene Mason, La Habra, CA (US)

(73) Assignee: CAREFUSION 303, INC., San Diego, CA (US)

( * ) Notice: Subject to any disclaimer, the term of this patent is extended or adjusted under 35 U.S.C. 154(b) by 213 days.

(21) Appl. No.: 16/403,399

(22) Filed: May 3, 2019

(65) Prior Publication Data
US 2020/0345935 A1 Nov. 5, 2020

(51) Int. Cl.
| A61M 5/19 | (2006.01) |
| A61M 5/14 | (2006.01) |
| A61M 5/315 | (2006.01) |
| A61M 39/24 | (2006.01) |
| A61M 5/178 | (2006.01) |

(52) U.S. Cl.
CPC ............ *A61M 5/19* (2013.01); *A61M 5/1409* (2013.01); *A61M 5/31513* (2013.01); *A61M 39/24* (2013.01); *A61M 2005/1787* (2013.01)

(58) Field of Classification Search
CPC .... A61M 5/19; A61M 5/1409; A61M 5/2033; A61M 5/31513; A61M 39/24; A61M 2005/1787; A61M 2005/2073; A61M 2005/31518; A61M 2005/3201; A61M 5/31596; A61M 5/1407; A61M 5/281; A61M 5/284; A61M 2005/3128; A61M 2005/31598
See application file for complete search history.

(56) References Cited

U.S. PATENT DOCUMENTS

| 5,599,312 A | 2/1997 | Higashikawa |
| 8,430,843 B2 * | 4/2013 | Chebator .......... A61M 5/31596 604/82 |
| 2011/0282381 A1 * | 11/2011 | Cronin ................ A61M 5/1407 606/213 |
| 2018/0221577 A1 | 8/2018 | Hopkins |

OTHER PUBLICATIONS

International Search Report and Written Opinion for Application No. PCT/US2020/031035, dated Jul. 17, 2020, 17 pages.

* cited by examiner

*Primary Examiner* — Shefali D Patel
(74) *Attorney, Agent, or Firm* — Morgan, Lewis & Bockius LLP

(57) ABSTRACT

A syringe includes a syringe body, a first plunger, a second plunger, and an inner tube. The syringe body defines a syringe port in fluid communication with a syringe cavity. The first plunger is disposed within the syringe cavity and defines a first chamber in the syringe cavity, wherein the first chamber is in fluid communication with the syringe port. The second plunger is disposed within the syringe cavity, the first plunger and the second plunger cooperatively defining a second chamber in the syringe cavity. The inner tube comprises an inner tube lumen, wherein the inner tube and a first plunger shaft lumen of a first plunger shaft define an annulus therebetween, the annulus in fluid communication with a first plunger channel of the first plunger and the annulus permits fluid communication between the syringe port and the first plunger channel.

13 Claims, 10 Drawing Sheets

MULTI-CHAMBER SYRINGE

FIELD OF THE INVENTION

The present disclosure generally relates to medication delivery systems, and, in particular, to syringes.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, a syringe. Certain configurations of IV sets may have extended lengths of tubing, for example, in excess of 6 feet. Additionally, tubing may be primed with saline prior to the infusion of a liquid medication.

In some applications, during the use of IV catheters, saline from the priming process may be delivered to patient before the liquid medication is delivered to the patient.

SUMMARY

The disclosed subject matter relates to syringes. In certain embodiments, a syringe is disclosed that comprises a syringe body defining a syringe cavity and a syringe port, wherein the syringe port is in fluid communication with the syringe cavity; a first plunger disposed within the syringe cavity and defining a first chamber in the syringe cavity, wherein the first chamber is in fluid communication with the syringe port, the first plunger comprising: a first plunger channel extending through the first plunger; a first plunger shaft extending from the first plunger, the first plunger shaft defining a first plunger shaft lumen, wherein the first plunger shaft lumen is in fluid communication with the first plunger channel; a second plunger disposed within the syringe cavity, the first plunger and the second plunger cooperatively defining a second chamber in the syringe cavity, the second plunger comprising: a second plunger shaft extending from the second plunger, the second plunger shaft defining a second shaft channel, the second shaft channel receiving at least a portion of the first plunger shaft; and an inner tube comprising an inner tube lumen, the inner tube extending from the syringe port into the first plunger shaft lumen, wherein the inner tube and the first plunger shaft lumen define an annulus therebetween, the annulus in fluid communication with the first plunger channel and the annulus permits fluid communication between the syringe port and the first plunger channel.

In certain embodiments, a medication delivery system is disclosed that comprises a syringe, comprising: a syringe body defining a syringe cavity and a syringe port, wherein the syringe port is in fluid communication with the syringe cavity; a first plunger disposed within the syringe cavity and defining a first chamber in the syringe cavity, wherein the first chamber is in fluid communication with the syringe port, the first plunger comprising: a first plunger channel extending through the first plunger; a first plunger shaft extending from the first plunger, the first plunger shaft defining a first plunger shaft lumen, wherein the first plunger shaft lumen is in fluid communication with the first plunger channel; a second plunger disposed within the syringe cavity, the first plunger and the second plunger cooperatively defining a second chamber in the syringe cavity, the second plunger comprising: a second plunger shaft extending from the second plunger, the second plunger shaft defining a second shaft channel, the second shaft channel receiving at least a portion of the first plunger shaft; and an inner tube comprising an inner tube lumen, the inner tube extending from the syringe port into the first plunger shaft lumen, wherein the inner tube and the first plunger shaft lumen define an annulus therebetween, the annulus in fluid communication with the first plunger channel and the annulus permits fluid communication between the syringe port and the first plunger channel; and a tubing defining a first flow path and a second flow path, wherein the first flow path is separated from the second flow path by a tubing wall, the first flow path is in fluid communication with the first chamber, and the second flow path is in fluid communication with the annulus.

In certain embodiments, a method to deliver medication is disclosed that comprises receiving saline from a return flow path of a tubing in an inner tube of a syringe; directing saline from the inner tube to an annulus of the syringe, wherein the inner tube and a medication plunger shaft lumen define the annulus therebetween; and directing saline from the annulus to a saline chamber of the syringe.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed syringe incorporates a multiple-plunger syringe with an inner tube disposed within a medication plunger shaft. Fluid can flow from the lumen of the inner tube and into the annulus formed between the inner tube and the medication plunger shaft lumen. By allowing fluid flow into the annulus, fluid, such as saline, can flow into the saline chamber when the medication plunger and the saline plunger are in any position while maintaining a compact profile.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid using the disclosed syringe, it is to be understood that this description is only an example of usage and does not limit the scope of the claims. Various aspects of the disclosed syringe may be used in any application where it is desirable to provide for the administration of medical fluids.

The disclosed syringe overcomes several challenges discovered with respect to certain conventional syringe. One challenge with certain conventional syringes is that syringes may deliver excess medical fluid, such as saline, to patients. Further, conventional syringes with multiple plungers may have a large profile. Because excess medical fluid may delay the delivery of medical fluids, may not be tolerated by fluid restricted patients, such as premature babies, and large profile syringes limit IV set configurations, the use conventional syringes is undesirable.

Therefore, in accordance with the present disclosure, it is advantageous to provide a syringe as described herein that eliminates or substantially reduces delivering excess medical fluid to a patient and reduces the overall profile of the syringe body. The disclosed syringe provides a tube-in-tube configuration that permits a reduced profile while reducing excess medical fluid delivered to the patient.

An example of a syringe that prevents delivery of excess medical fluid is now described.

Figure 1:
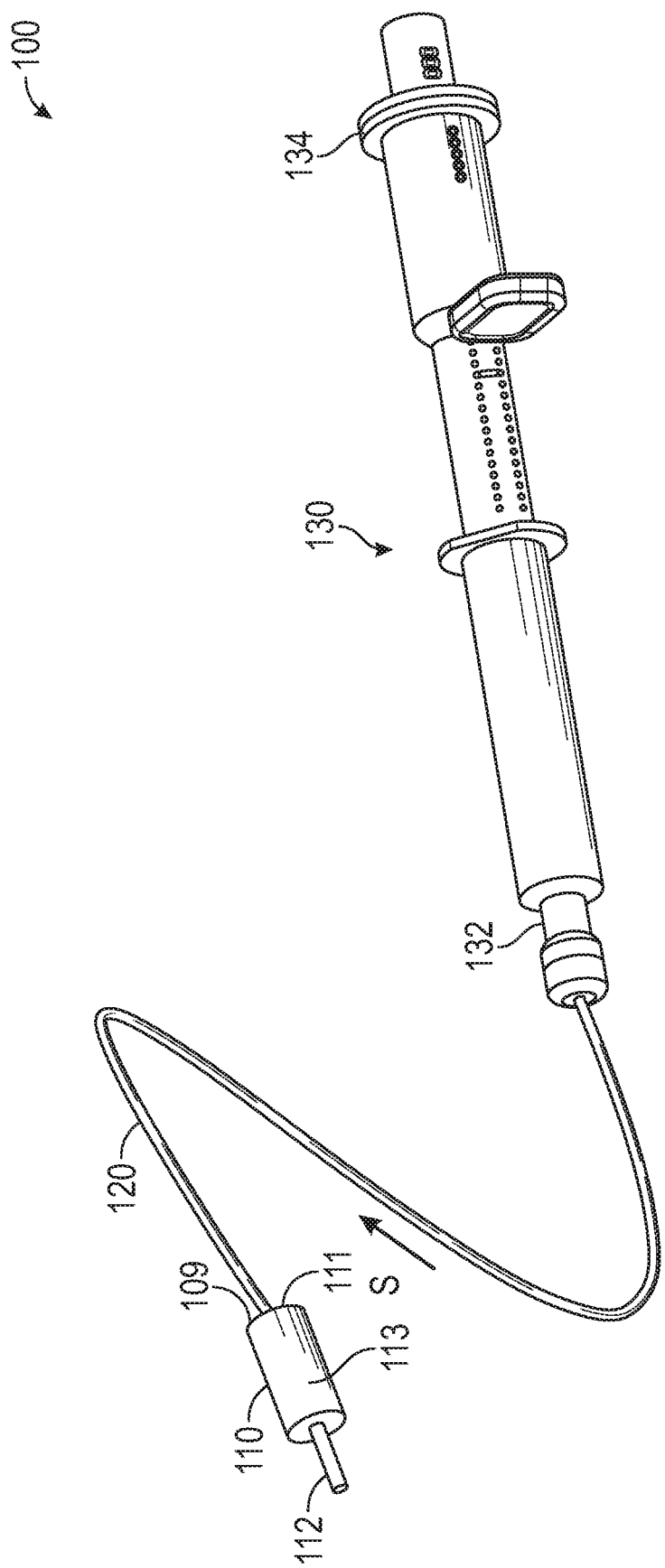
FIG. 1 is a perspective view of a medication delivery system, in accordance with various aspects of the present disclosure.

FIG. 1 is a perspective view of a medication delivery system 100, in accordance with various aspects of the present disclosure. In the illustrated example, the medication delivery system 100 delivers medication from the syringe 130 to the patient via a catheter 112 without delivering excess fluid, such as saline, used to prime the medication delivery system 100.

In some embodiments, a medication flow path within a dual lumen tubing 120 can be primed with saline to remove any air or trapped gasses within the medication flow path of the dual lumen tubing 120. Saline can be advanced from a proximal end 132 of the syringe 130, through the medication flow path of the dual lumen tubing 120 and to the valve 110.

The saline from the medication flow path of the dual lumen tubing 120 can be received by the medication flow path 111 of the valve 110. In a priming configuration, a valve element 113 can prevent saline from the medication flow path 111 from entering the patient catheter 112 and can instead direct the saline toward the return flow path 109 of the valve 110 to allow primed saline to be returned to the syringe 130 via the return flow path of the dual lumen tubing 120.

Figure 2:
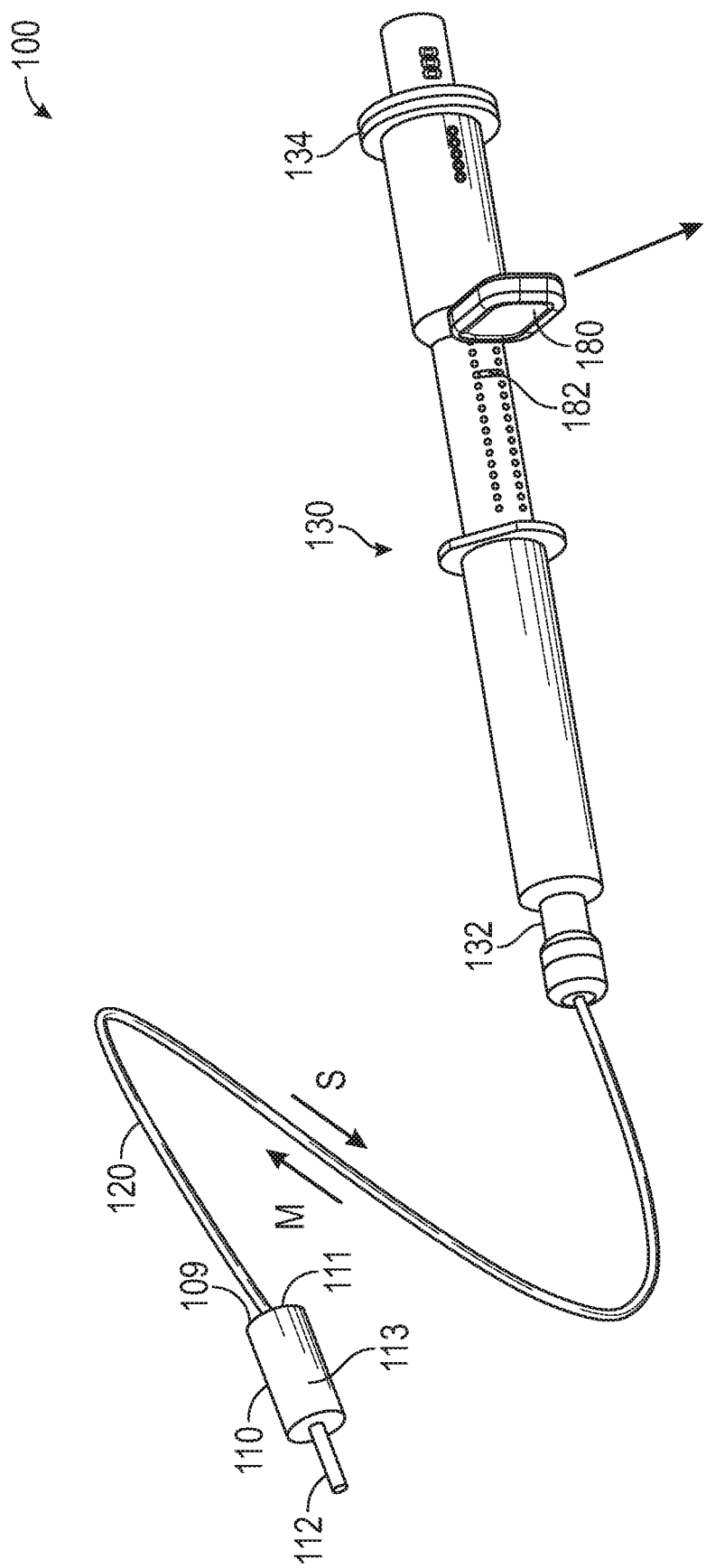
FIG. 2 is a perspective view of the medication delivery system of FIG. 1 with the priming trigger removed, in accordance with various aspects of the present disclosure.

FIG. 2 is a perspective view of the medication delivery system 100 of FIG. 1 with the priming trigger 180 removed, in accordance with various aspects of the present disclosure. In the illustrated example, the syringe 130 advances medication within the medication flow path of the dual lumen tubing 120 to prime the medication flow path of the dual lumen tubing 120. Advantageously, by priming the medication flow path with medication, the medication can be delivered to the patient via the catheter 112 proximal to the patient with less delay and without delivering the saline used to prime the medication flow path of the dual lumen tubing 120.

To introduce medication into the medication flow path of the dual lumen tubing 120, the medication plunger within the syringe 130 can be advanced or otherwise displaced to introduce a volume of medication into the medication flow path of the dual lumen tubing 120. Optionally, the medication plunger of the syringe 130 can be configured to be advanced or displaced a desired amount to dispense a volume of medication into the medication flow path of the dual lumen tubing 120 that is equivalent to the volume of the medication flow path of the dual lumen tubing 120. In other words, medication plunger of the syringe 130 can be advanced to fill the volume of the medication flow path of the dual lumen tubing 120 up to the valve element 113 to prime the medication for administration via the catheter 112.

In some embodiments, the priming of medication into the medication flow path of the dual lumen tubing 120 can be automated or otherwise simplified. For example, the medication plunger can be biased to be advanced to introduce medication into the medication flow path of the dual lumen tubing 120. The biasing member of the priming mechanism within the syringe 130 can be released by removing the priming trigger 180. By removing the priming trigger 180, the biasing member can advance the medication plunger to prime the medication within the medication delivery system 100. Optionally, the priming travel of the medication plunger can be stopped or limited by a priming stop 182. By limiting the travel of the medication plunger during priming, a desired volume of medication can be introduced into the medication flow path of the dual lumen tubing 120, for example, sufficient medication volume to fill the medication flow path of the dual lumen tubing 120.

As illustrated, as the medication is introduced into the medication flow path of the dual lumen tubing 120, the saline previously primed through the dual lumen tubing 120 is displaced. The displaced saline is directed by the valve element 113 through the return flow path 109 of the valve 110 and into the return flow path of the dual lumen tubing 120.

Medical fluid from the return flow path of the dual lumen tubing 120 can be returned into the syringe 130. Returned medical fluid such as saline can be introduced into a return or saline chamber of the syringe 130.

Figure 3:
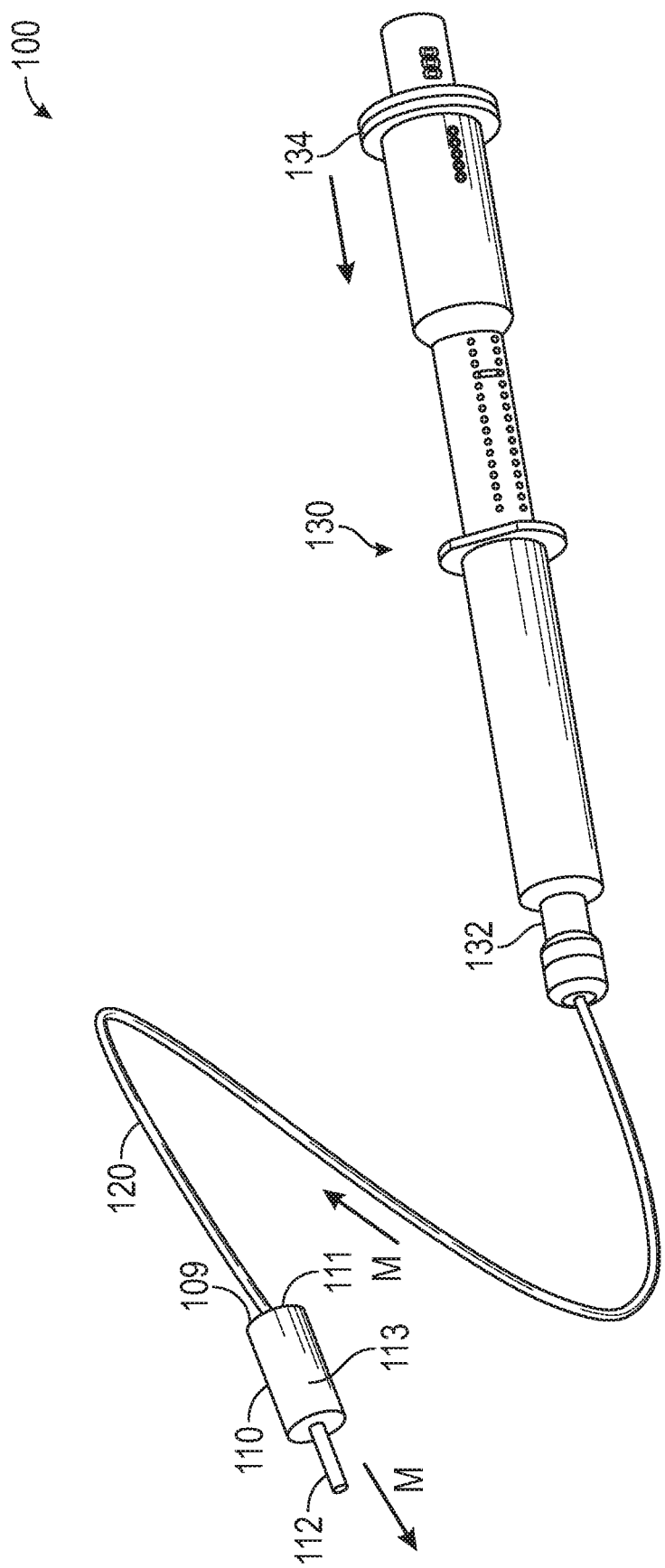
FIG. 3 is a perspective view of the medication delivery system of FIG. 1 with the syringe actuated, in accordance with various aspects of the present disclosure.

FIG. 3 is a perspective view of the medication delivery system 100 of FIG. 1 with the syringe 130 actuated, in accordance with various aspects of the present disclosure. In the illustrated example, the syringe 130 is actuated to dispense medication to the patient through the catheter 112.

As illustrated, the distal end 134 of the syringe 130 can be advanced toward the proximal end 132 of the syringe 130 to actuate the medication plunger within the syringe 130. By actuating the syringe 130, the medication plunger can be advanced to deliver medication from the syringe 130 into the medication flow path of the dual lumen tubing 120. In some embodiments, the syringe 130 can be actuated by a syringe pump to control the flow of medication to the patient.

During operation, the valve 110 is actuated to permit the flow of medication from the medication flow path 111 of the valve 110 to the patient via the catheter 112. In some embodiments, the valve element 113 is actuated to permit fluid communication between the medication flow path 111 and the catheter 112 to allow medication to flow to the patient. Optionally, the valve 110 can be located proximal to the patient to minimize the length of the catheter 112, reduce the amount of saline administered to the patient, and reduce the delivery time for the medication.

Figure 4:
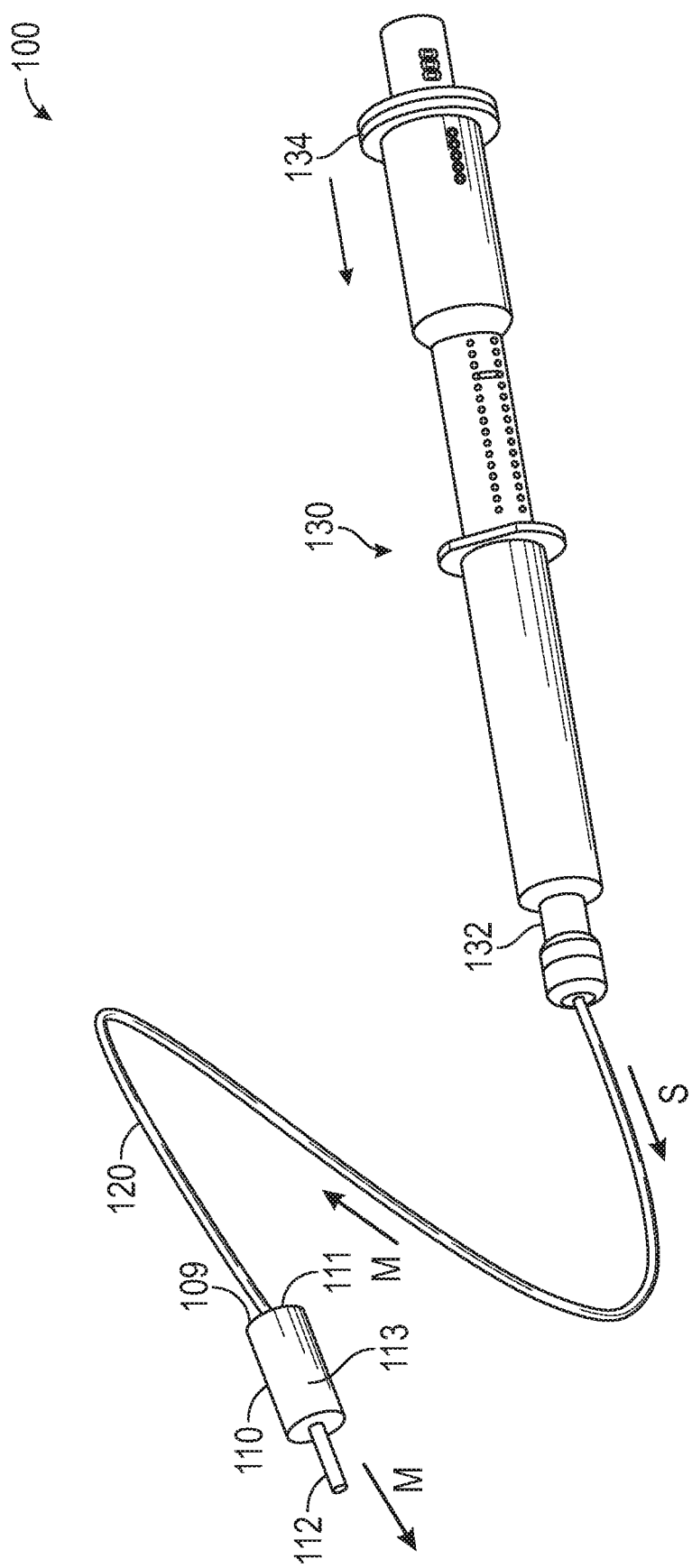
FIG. 4 is a perspective view of the medication delivery system of FIG. 1 with the syringe actuated, in accordance with various aspects of the present disclosure.

FIG. 4 is a perspective view of the medication delivery system 100 of FIG. 1 with the syringe 130 actuated, in accordance with various aspects of the present disclosure. In the illustrated example, the syringe 130 advances saline through the medication flow path of the dual lumen tubing 120 to advance the remaining medication to the patient via the catheter 112.

As illustrated, after the medication is expelled from the syringe 130, medication may remain in the volume of the medication flow path of the dual lumen tubing 120. To ensure that the medication is fully delivered to the patient, the syringe 130 can be utilized to administer a saline "push" to continue to advance the medication through the medication flow path of the dual lumen tubing 120 after the medication within the syringe 130 is exhausted. Optionally, saline can be administered through the medication flow path until the medication is fully administered to the patient.

Figure 5:
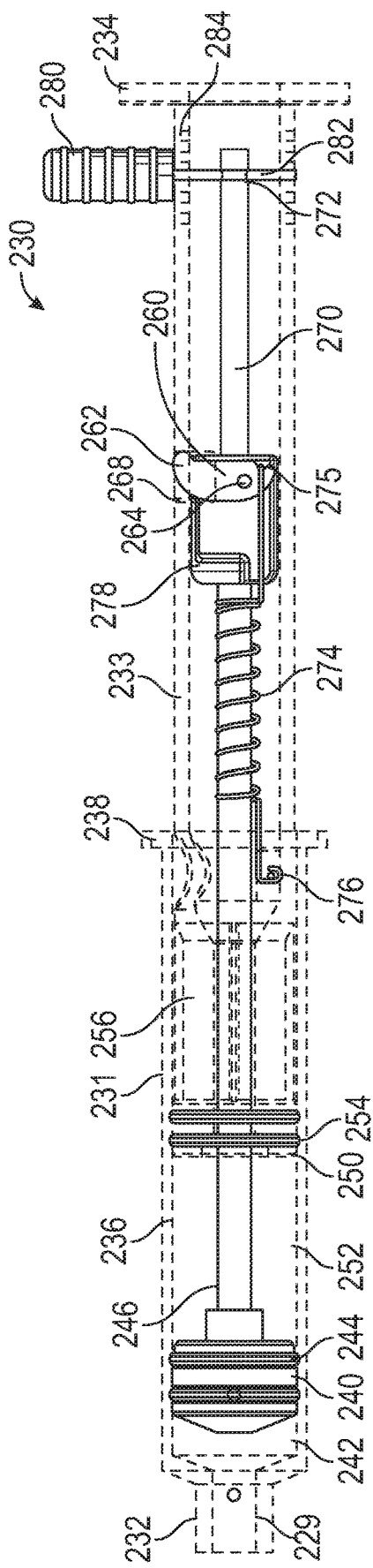
FIG. 5 is an elevation view of a syringe with the syringe body hidden, in accordance with various aspects of the present disclosure.

FIG. 5 is an elevation view of a syringe 230 with the syringe body hidden, in accordance with various aspects of the present disclosure. In the figures, similar features may be referred to with similar reference numerals. In the depicted example, the syringe 230 can be utilized to dispense medication and/or saline through a tubing coupled to the syringe port 229 of the syringe 230. As illustrated, the syringe 230 can receive, store, and/or dispense medication and/or saline in chambers defined therein.

As illustrated, the proximal syringe portion 231 of the syringe 230 can store medical fluids such as medication and saline in a syringe cavity 236. In the illustrated embodiment, the medication plunger 240 is movable within the syringe cavity 236 to define a medication chamber 242 within the proximal syringe portion 231. Optionally, the volume of the medication chamber 242 is defined by the position of the medication plunger 240 relative to the proximal end 232 of the syringe 230. In the depicted example, the medication chamber 242 can store medication.

In some embodiments, the medication chamber 242 is in fluid communication with the syringe port 229 of the syringe 230. Optionally, the medication plunger 240 can include one or more seals 244 to seal against the walls of the syringe cavity 236 to prevent unintended fluid migration or mixing.

Further, the medication plunger 240 can be moved by the medication plunger shaft 246. In some embodiments, the medication plunger 240 can be drawn distally to expand the medication chamber 242 and draw in more medication or medical fluid through the syringe port 229. In some embodiments, the medication plunger 240 can be advanced proximally to contract the medication chamber 242 and expel medication or medical fluid from the medication chamber 242 through the syringe port 229.

In the illustrated embodiment, the saline plunger 250 is movable within the syringe cavity 236 to define a saline chamber 252 within the proximal syringe portion 231. In some embodiments, the saline plunger 250 and the medication plunger 240 cooperatively define the saline chamber 252 within the syringe cavity 236. Optionally, the volume of the saline chamber 252 is defined by the position of the medication plunger 240 and the saline plunger 250. In the depicted example, the saline chamber 252 can store saline or other medical fluids.

Optionally, the saline plunger 250 can include one or more seals 254 to seal against the walls of the syringe cavity 236 to prevent unintended fluid migration or mixing.

Further, the saline plunger 250 can be moved by the saline plunger shaft 256. In some embodiments, the saline plunger 250 can be drawn distally to expand the saline chamber 252 and draw in more saline or medical fluid. In some embodiments, the saline plunger 250 can be advanced proximally to contract the saline chamber 252 and expel saline or medical fluid from the saline chamber 252.

As previously described, during the administration of medication to patients, for example, fluid restricted patients, medication can be dispensed from the medication chamber 242 and then saline can be dispensed from the saline chamber 252 to advance the medication remaining in the tubing.

In the depicted example, medication can be dispensed from the syringe 230 by advancing the medication plunger 240 within the syringe cavity 236. As a result, medication can be delivered from the syringe 230 through the syringe port 229.

In some embodiments, the syringe 230 can include a priming mechanism or actuation mechanism 270 to automate, control, or otherwise simplify advancement of the medication plunger 240 to facilitate the priming of medication into an IV tubing. Optionally, the actuation mechanism 270 can be configured to introduce a sufficient volume of medication from the medication chamber 242 into the IV tubing to fully fill or prime the IV line prior to administration of the medication to the patient.

In the illustrated embodiment, the actuation mechanism 270 can utilize a biasing member such as a tension spring 274 to advance the medication plunger 240 within the syringe cavity 236.

Optionally, the tension spring 274 can be coupled to the proximal syringe portion 231 at the proximal end 276 of the tension spring 274 and coupled to the actuation mechanism 270 at the distal end 275 of the tension spring 274. In some embodiments, the actuation mechanism 270 extends from, or is generally coupled to the medication plunger shaft 246. Further, the tension spring 274 can be disposed around the medication plunger shaft 246.

As illustrated, the tension spring 274 can be preloaded or biased to facilitate advancement of the medication plunger 240 upon release or activation of the tension spring 274. In the depicted example, the tension spring 274 can be extended or biased from a resting length to an elongated tensioned length. In some embodiments, a biasing member can be compressed from a resting length to a shortened compressed length.

As illustrated, the tension spring 274 can be preloaded or elongated by retracting the actuation mechanism 270, which extends the tension spring 274. In some embodiments, the actuation mechanism 270 can be locked or retained in place, preventing the medication plunger 240 from being advanced prior to priming by a retention mechanism. In the illustrated embodiment, the retention mechanism includes a priming trigger 280 with a shaft 282 that extends through the distal syringe portion 233 and through the through hole 272 of the actuation mechanism 270, releasably coupling the actuation mechanism 270 to the distal syringe portion 233. The priming trigger 280 can extend through slot 284 of the distal syringe portion 233.

Optionally, the tension applied to the tension spring 274 can be adjusted by altering the position of the actuation mechanism 270 relative to the distal syringe portion 233 and inserting the priming trigger 280 through a slot 284 aligned with the through hole 272 of the actuation mechanism 270. In some embodiments of the present disclosure, a distal end 275 of the tension spring 274 is connected to a priming stop 278 by engaging a rotating member 260, which rotates about a pivot point 264, that includes a contact 262 that engages slot 268.

Figure 6:
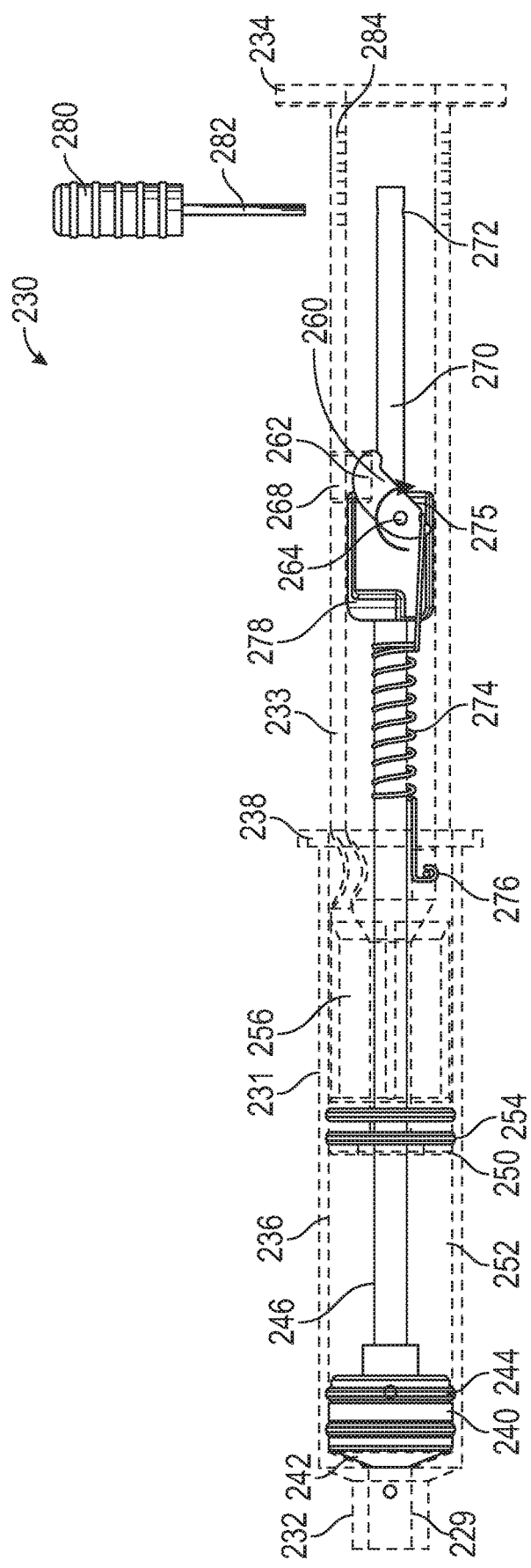
FIG. 6 is an elevation view of the syringe of FIG. 5 with the syringe body hidden and the priming trigger removed, in accordance with various aspects of the present disclosure.

FIG. 6 is an elevation view of the syringe 230 of FIG. 5 with the syringe body hidden and the priming trigger 280 removed, in accordance with various aspects of the present disclosure. As illustrated, the priming mechanism of the syringe 230 can be activated by removing the priming trigger 280 from the syringe 230.

By removing the priming trigger 280, the tension spring 274 is allowed to contract to advance the medication plunger shaft 246 and in turn, the medication plunger 240. By advancing the medication plunger 240, medication within the medication chamber 242 can advance through the IV tubing and prime the IV tubing. As described herein, the medication plunger 240 can be advanced by a desired or predetermined amount corresponding to the IV tubing volume during the priming process.

Figure 7:
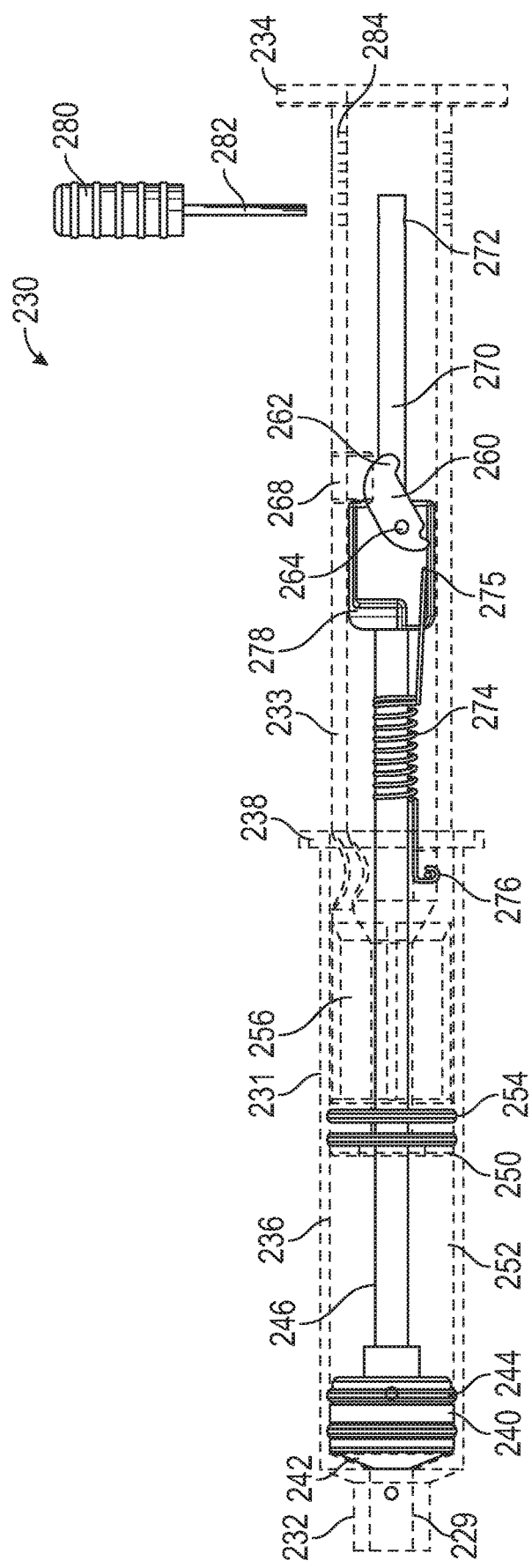
FIG. 7 is an elevation view of the syringe of FIG. 5 with the syringe body hidden and the priming mechanism actuated, in accordance with various aspects of the present disclosure.

FIG. 7 is an elevation view of the syringe 230 of FIG. 5 with the syringe body hidden and the priming mechanism actuated, in accordance with various aspects of the present disclosure. In the illustrated embodiment, the medication plunger 240 can be further actuated to administer any remaining medication in the medication chamber 242 into the IV tubing and to the patient. In some embodiments, the medication plunger shaft 246 can be actuated to advance the medication plunger 240. For example, the distal end 234 of the distal syringe portion 233 can be advanced toward the proximal end 232 to advance the medication plunger 240. In some embodiments, the extensions 238 of the proximal syringe portion 231 can allow a clinician or a syringe pump to advance the distal syringe portion 233 relative to the proximal syringe portion 231.

Figure 8:
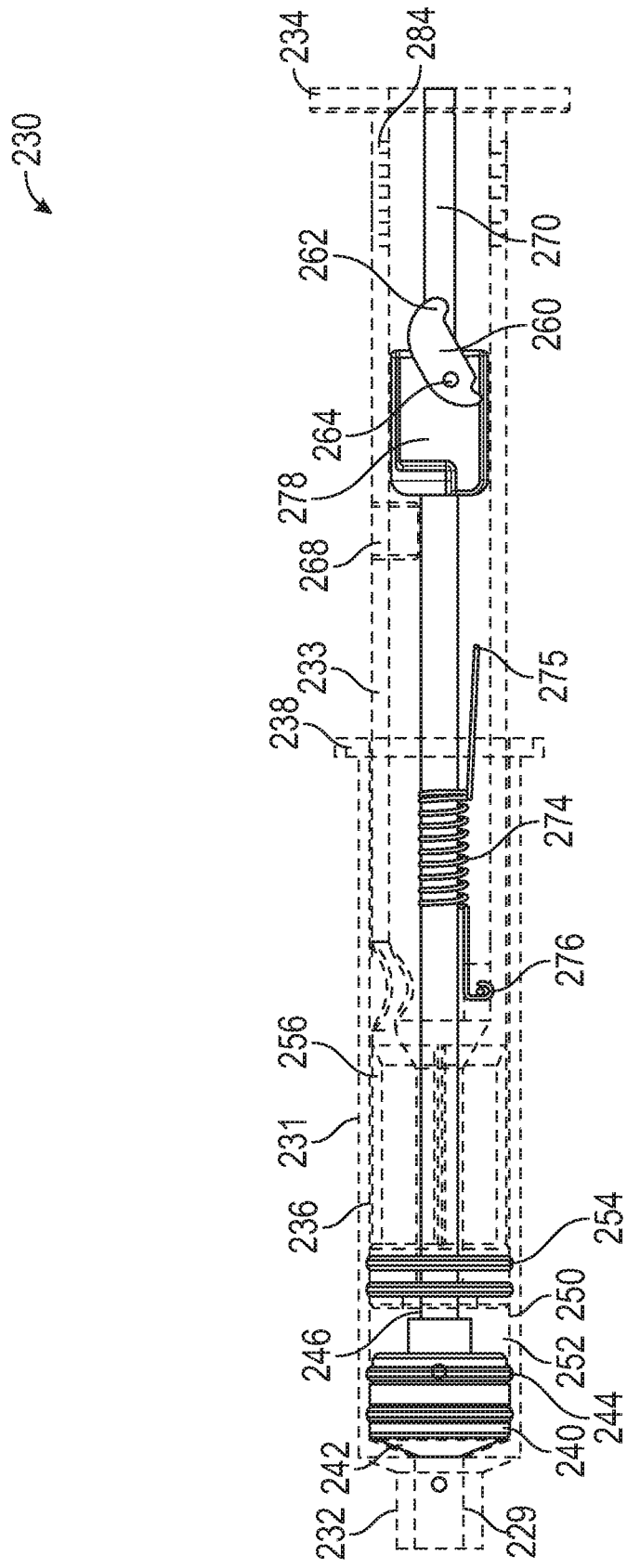
FIG. 8 is an elevation view of the syringe of FIG. 5 with the syringe body hidden and the syringe actuated, in accordance with various aspects of the present disclosure.

FIG. 8 is an elevation view of the syringe 230 of FIG. 5 with the syringe body hidden and the syringe actuated, in accordance with various aspects of the present disclosure. In the illustrated embodiment, the saline plunger 250 can be actuated to administer saline from the saline chamber 252 into the IV tubing to "push" or deliver any remaining medication in the IV tubing to the patient. In some embodiments, the saline plunger shaft 256 can be actuated to advance the saline plunger 250. In some embodiments, the same actuation method for the medication plunger 240 can be utilized for actuating the saline plunger 250.

For example, the distal end 234 of the distal syringe portion 233 can be advanced toward the proximal end 232 to advance the saline plunger 250. In some embodiments, the extensions 238 of the proximal syringe portion 231 can allow a clinician or a syringe pump to advance the distal syringe portion 233 relative to the proximal syringe portion 231.

In some embodiments, saline from the saline chamber 252 can be advanced through or around the medication chamber 242 to exit the syringe 230 via the syringe port 229. For example, as the saline plunger 250 is advanced, saline can advanced through a saline bypass inlet port 253, through a bypass path 255 and introduced into the syringe port 229 via a saline bypass outlet port 255 (shown schematically) to allow saline to be administered by the syringe 230. In some embodiments, the bypass path 255 can include a check valve 257 (shown schematically) to prevent the backflow of medication from the medication chamber 242 into the saline chamber 252 if the saline bypass inlet port 253 is uncovered during the administration of medication. In some embodiments, the bypass path 255 and the check valve 257 can be integrated in a bypass adapter coupled to the syringe 230.

Figure 9:
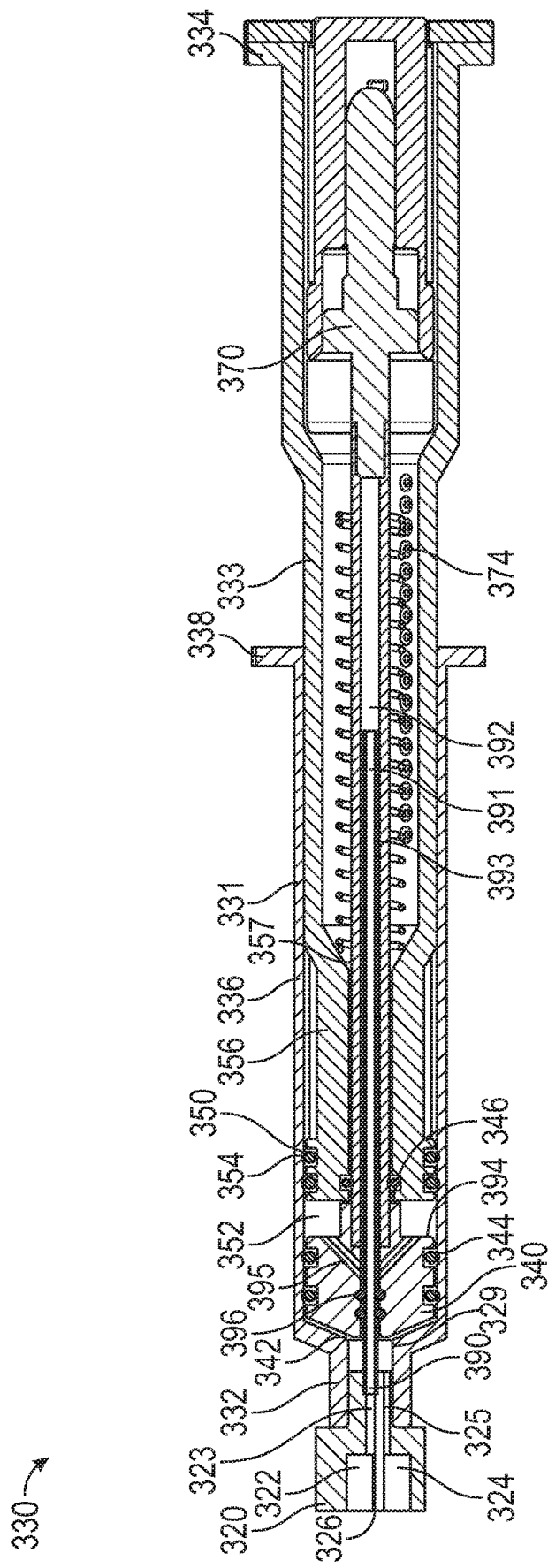
FIG. 9 is a cross sectional view of a syringe, in accordance with various aspects of the present disclosure.

FIG. 9 is a cross sectional view of a syringe 330, in accordance with various aspects of the present disclosure. In the depicted example, the syringe 330 can be utilized to dispense medication and/or saline through dual lumen tubing 320 coupled to the syringe port 329 of the syringe 330. As illustrated, the syringe 330 can receive, store, and/or dispense medication and/or saline to and from the dual lumen tubing 320 in a compact design utilizing a tube-in-tube configuration described herein.

As previously described with respect to syringe 230, the syringe 330 includes a proximal syringe portion 331 and a distal proximal syringe portion 333. The proximal syringe portion 331 can store medical fluids such as medication and saline in the syringe cavity 336. For example, the syringe 330 can store medication in a medication chamber 342 defined by a moveable medication plunger 340. In the depicted example, the medication plunger 340 can be moved by actuating the medication plunger shaft 346. In some embodiments of the present disclosure, the proximal syringe portion 331 comprises an extension 338. Further, the syringe 330 can store saline in a saline chamber 353 defined by a movable saline plunger 350. Similarly, the saline plunger 350 can be moved by actuating the saline plunger shaft 356. As illustrated, at least a portion of the medication plunger shaft 346 can extend through the saline plunger 350 and the saline plunger shaft 356 via a shaft channel 357 formed therethrough. In some embodiments, the medication plunger shaft 346 can seal against the shaft channel 357 of the saline plunger 350 to prevent the migration or mixing of medical fluids. Optionally, the medication plunger shaft 346 can be concentrically disposed within the shaft channel 357. In some embodiments of the present disclosure, any of the medication plunger 340 and/or the saline plunger 350 can include a seal configured to seal against another portion of the syringe 330. In some embodiments, the medication plunger 340 can include one or more seals 344 to seal against a wall of the syringe cavity 336 to prevent unintended fluid migration or mixing. In some embodiments, the saline plunger 350 can include one or more seals 354 to seal against a wall of the syringe cavity 336 to prevent unintended fluid migration or mixing.

As illustrated, the dual lumen tubing 320 can be coupled to the proximal end 332 of the syringe 330 permitting fluid communication between the dual lumen tubing 320 and the syringe 330. In some embodiments, the medication flow path 324 is placed in fluid communication with the syringe port 329 via the medication flow port 325. The medication flow path 324 can be in fluid communication with the medication chamber 342. Further, in some embodiments, the return flow path 322 is placed into fluid communication with the inner tube 390 via the return flow port 323. The return flow path 322 can be in communication with the saline chamber 352 via the inner tube 390. Optionally, a tubing wall 326 within the dual lumen tubing 320 can divide the medication flow path 324 and the return flow path 322. In some embodiments, the dual lumen tubing 320 is of a longer length than a downstream catheter.

During operation, medication can be dispensed from the syringe 330 into the dual lumen tubing 320 by advancing the medication plunger 340 within the syringe cavity 336. As a result, medication can be dispensed from the medication chamber 342 into the medication flow path 324 of the dual lumen tubing 320. Medication can be dispensed from the syringe 330 during a priming procedure or during administration as described herein.

In some embodiments, the actuation mechanism 370 can utilize a biasing member such as spring 374 to advance the medication plunger 340 within the syringe cavity 336. In the depicted example, the spring 274 can be compressed or biased from a resting length to a shortened compressed length. During operation, the spring 374 can be allowed to extend toward the natural length of the spring 374 to advance the medication plunger 340. In some embodiments of the present disclosure, the actuation mechanism 370 is adjacent distal end 334 of the distal syringe portion 333.

As previously described, as medication is introduced into the dual lumen tubing 320, saline can be returned to the syringe 330. For example, saline can be received from the return flow path 322 of the dual lumen tubing 320 into the saline chamber 352. In the depicted example, the inner tube 390 extends into the return flow port 323 to permit return flow from the return flow path 322 into the inner tube lumen 391.

As illustrated, the inner tube 390 extends distally from the syringe port 329 and into the shaft lumen 392 of the medication plunger shaft 346. Further, the inner tube 390 can extend across the medication chamber 342 and through the medication plunger 340 to enter the shaft lumen 392 of the medication plunger shaft 346. Optionally, the medication plunger shaft 346 is moveable relative to the inner tube 390. In some embodiments, the inner tube 390 passes through a plunger channel 395 extending through the medication plunger 340. Optionally, the inner tube 390 can seal against the plunger channel 395 via sealing members 396 disposed therebetween.

Figure 10:
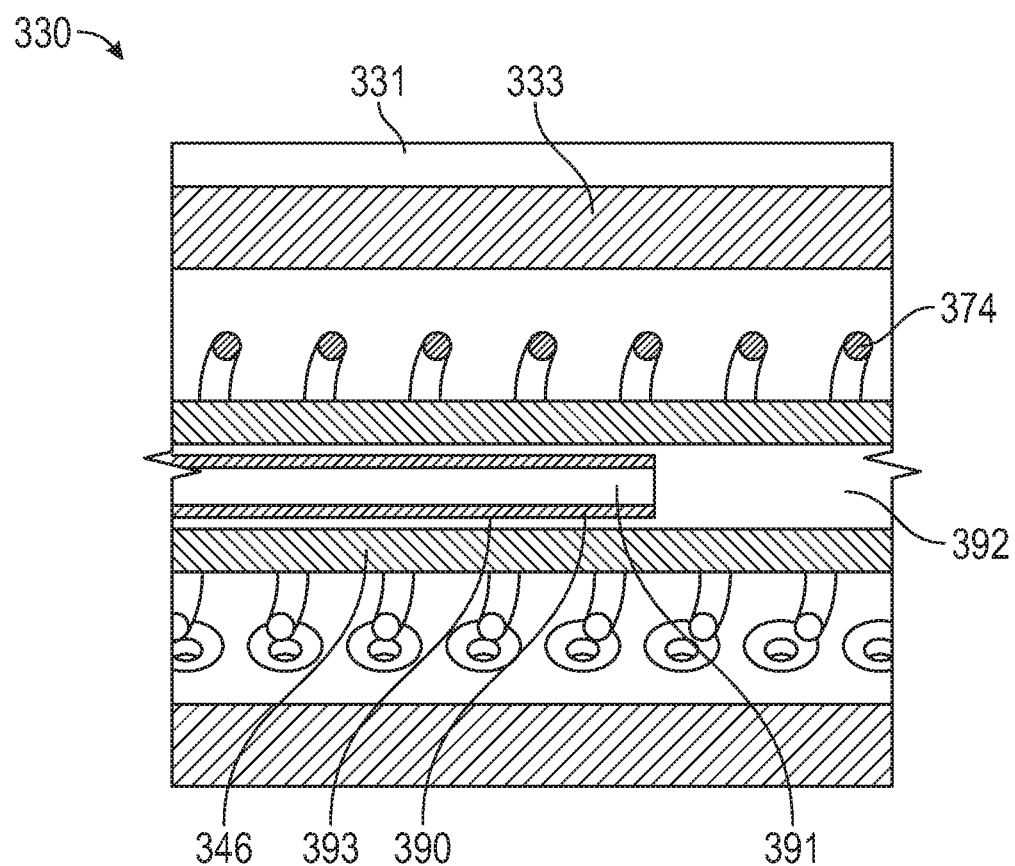
FIG. 10 is a cross sectional detail view of the syringe of FIG. 9, in accordance with various aspects of the present disclosure.

FIG. 10 is a cross sectional detail view of the syringe 330 of FIG. 9, in accordance with various aspects of the present disclosure. With reference to FIGS. 9 and 10, during operation, return flow of saline from the return flow path 322 is received by the inner tube lumen 391 and is directed within the inner tube 390 to flow into the shaft lumen 392 of the medication plunger shaft 346. In the illustrated embodiment, return flow from the inner tube 390 flows into an annulus 393 defined between an outer surface of the inner tube 390 and an inner surface of the shaft lumen 392 of the medication plunger shaft 346. Advantageously, by defining the flow path of the annulus 393 with the inner tube 390 and the shaft lumen 392, the syringe 330 is able to maintain a flow path between the return flow path 322 and the saline chamber 352 regardless of the position of the medication plunger 340 and/or the saline plunger 350. Further, the use of the annulus 393 as a flow path allows for a compact tube-in-tube configuration.

With reference back to FIG. 9, in the illustrated embodiment, the defined annulus 393 allows return flow from the return flow path 322 to be delivered to the saline chamber 352. In the depicted example, the annulus 393 directs return flow proximally toward the medication plunger 340. Optionally, the defined annulus 393 can continue in the flow path between the outer surface of the inner tube 390 and the inner surface of the plunger channel 395, providing fluid communication therebetween.

In the illustrated embodiment, the medication plunger 340 includes one or more saline ports 394 to direct return flow from the annulus 393 to the saline chamber 352. In some embodiments, the saline ports 394 are formed in the distal portion of the medication plunger 340 and extend from the plunger channel 395 to a distal surface of the medication plunger 340. Advantageously, by directing return flow to the saline chamber 352 via the saline ports 394, the syringe 330 is able to contain a volume of saline within the saline chamber 352 independent of the location of the medication plunger 340 and/or the saline plunger 350. In some embodiments, the sealing members 396 prevent return flow from migrating out of the saline chamber 352 unintentionally.

As described herein, in some applications, saline may be dispensed from the syringe 330 to the medication flow path 324 of the dual lumen tubing 320 to "push" or advance medication within the medication flow path 324 toward the patient. In some embodiments, saline can be dispensed from the saline chamber 352 by advancing the saline plunger 350 toward the proximal end 332 of the syringe 330.

Optionally, saline from the saline chamber 352 can be advanced past the medication plunger 340 to allow the saline to be administered by the syringe 330 via the medication flow path 324. In some embodiments, as the saline plunger 350 is advanced, saline can be directed through the saline ports 394 and into the plunger channel 395.

In some embodiments, the sealing members 396 in the plunger channel 395 are configured as check valves to permit fluid flow from the saline chamber 352 to the medication chamber 342 while preventing back flow from the medication chamber 342 to the saline chamber 352. The sealing members 396 may include geometric features or valve structures to permit one-way flow. For example, sealing members 396 may include elements that move to allow flow into the medication chamber 342. Optionally, the sealing members 396 may permit flow from the saline chamber 352 into the medication chamber 342 in response to a predetermined pressure applied by advancing the saline plunger 350. Therefore, during operation, saline can flow from the medication chamber 342 into the medication flow path 324 of the dual lumen tubing 320.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A syringe comprising:
   a syringe body defining a syringe cavity and a syringe port, wherein the syringe port is in fluid communication with the syringe cavity;
   a first plunger disposed within the syringe cavity and defining a first chamber in the syringe cavity, wherein the first chamber is in fluid communication with the syringe port, the first plunger comprising a first plunger channel extending through the first plunger;
   a first plunger shaft extending from the first plunger, the first plunger shaft defining a first plunger shaft lumen, wherein the first plunger shaft lumen is in fluid communication with the first plunger channel;
   a second plunger disposed within the syringe cavity, the first plunger and the second plunger are movable relative to each other and the first plunger, the second plunger, and the syringe cavity cooperatively define a second chamber;
   a second plunger shaft extending from the second plunger, the second plunger shaft defining a second shaft channel, the second shaft channel receiving at least a portion of the first plunger shaft; and
   an inner tube comprising an inner tube lumen, the inner tube extending from the syringe port into the first plunger shaft lumen, wherein the inner tube and the first plunger shaft lumen define an annulus therebetween, the annulus in fluid communication with the first plunger channel and the annulus permits fluid communication between the syringe port and the first plunger channel.

2. The syringe of claim 1, wherein the first plunger further comprises at least one first plunger port, the at least one first plunger port extending from the first plunger channel to the second chamber, wherein the at least one first plunger port permits fluid communication between the syringe port and the second chamber.

3. The syringe of claim 2, wherein the first plunger further comprises at least one check valve disposed within the first plunger channel, wherein the at least one check valve permits fluid flow from the second chamber to the first chamber and prevents fluid flow from the first chamber to the second chamber.

4. The syringe of claim 1, wherein the first plunger further comprises at least one check valve disposed within the first plunger channel, wherein the at least one check valve permits fluid flow from the annulus to the first chamber and prevents fluid flow from the first chamber to the annulus.

5. The syringe of claim 1, wherein the first plunger comprises a sealing member configured to engage against the syringe cavity.

6. The syringe of claim 1, wherein the second plunger comprises a sealing member configured to engage against the syringe cavity.

7. The syringe of claim 1, wherein the first plunger shaft comprises a sealing member configured to engage against the second shaft channel.

8. The syringe of claim 1, wherein the inner tube is movable relative to the first plunger shaft.

9. A medication delivery system comprising:
a syringe comprising:
 a syringe body defining a syringe cavity and a syringe port, wherein the syringe port is in fluid communication with the syringe cavity;
 a first plunger disposed within the syringe cavity and defining a first chamber in the syringe cavity, wherein the first chamber is in fluid communication with the syringe port, the first plunger comprising a first plunger channel extending through the first plunger;
 a first plunger shaft extending from the first plunger, the first plunger shaft defining a first plunger shaft lumen, wherein the first plunger shaft lumen is in fluid communication with the first plunger channel;
 a second plunger disposed within the syringe cavity, the first plunger and the second plunger are movable relative to each other and the first plunger, the second plunger, and the syringe cavity cooperatively define a second chamber;
 a second plunger shaft extending from the second plunger, the second plunger shaft defining a second shaft channel, the second shaft channel receiving at least a portion of the first plunger shaft; and
 an inner tube comprising an inner tube lumen, the inner tube extending from the syringe port into the first plunger shaft lumen, wherein the inner tube and the first plunger shaft lumen define an annulus therebetween, the annulus in fluid communication with the first plunger channel and the annulus permits fluid communication between the syringe port and the first plunger channel; and
a tubing defining a first flow path and a second flow path, wherein the first flow path is separated from the second flow path by a tubing wall, the first flow path is in fluid communication with the first chamber, and the second flow path is in fluid communication with the annulus.

10. The medication delivery system of claim 9, wherein the tubing comprises a first port in fluid communication with the first flow path and the syringe port.

11. The medication delivery system of claim 9, wherein the tubing comprises a second port in fluid communication with the second flow path and the inner tube.

12. The medication delivery system of claim 9, wherein the first plunger further comprises at least one first plunger port, the at least one first plunger port extending from the first plunger channel to the second chamber, wherein the at least one first plunger port permits fluid communication between the second flow path and the second chamber.

13. The medication delivery system of claim 12, wherein the first plunger further comprises at least one check valve disposed within the first plunger channel, wherein the at least one check valve permits fluid flow from the second chamber to the first chamber and prevents fluid flow from the first chamber to the second chamber.

* * * * *